(12) United States Patent
Johnson et al.

(10) Patent No.: US 7,097,357 B2
(45) Date of Patent: Aug. 29, 2006

(54) METHOD AND SYSTEM FOR IMPROVED CORRECTION OF REGISTRATION ERROR IN A FLUOROSCOPIC IMAGE

(75) Inventors: Douglas Karl Johnson, Seabrook, NH (US); Lewis J. Levine, Weston, MA (US)

(73) Assignee: General Electric Company, Schenectady, NY (US)

( * ) Notice: Subject to any disclaimer, the term of this patent is extended or adjusted under 35 U.S.C. 154(b) by 121 days.

(21) Appl. No.: 10/859,767

(22) Filed: Jun. 2, 2004

(65) Prior Publication Data

US 2005/0281385 A1 Dec. 22, 2005

(51) Int. Cl.
*G01D 18/00* (2006.01)

(52) U.S. Cl. ...................... 378/205; 378/163
(58) Field of Classification Search ................ 378/205, 378/207, 163, 20, 197–198, 195; 600/426–427
See application file for complete search history.

(56) References Cited

U.S. PATENT DOCUMENTS

| | | | |
|---|---|---|---|
| 5,829,444 A | 11/1998 | Ferre et al. | |
| 5,951,475 A | 9/1999 | Gueziec et al. | |
| 6,285,902 B1 * | 9/2001 | Kienzle et al. | 600/427 |
| 6,301,495 B1 | 10/2001 | Gueziec et al. | |
| 6,470,207 B1 | 10/2002 | Simon et al. | |
| 6,484,049 B1 | 11/2002 | Seeley et al. | |
| 6,490,475 B1 * | 12/2002 | Seeley et al. | 600/426 |
| 6,621,491 B1 * | 9/2003 | Baumrind et al. | 345/419 |
| 6,652,142 B1 | 11/2003 | Launay et al. | |
| 6,920,347 B1 * | 7/2005 | Simon et al. | 600/424 |

* cited by examiner

*Primary Examiner*—Edward J. Glick
*Assistant Examiner*—Hoon Song
(74) *Attorney, Agent, or Firm*—McAndrews, Held & Malloy, Ltd.; Peter J. Vogel; Michael A. Dellapenna (57) ABSTRACT

Certain embodiments of the present invention provide a method and system for improved registration of image and navigation references used in image-guided operations. Certain embodiments of the system include an image acquisition device for obtaining at least one image of an object, a first calibration fixture positioned in relation to the image acquisition device, and a second calibration fixture positioned in relation to the object. The position data from first calibration fixture is used to form a characterization of the image acquisition device, which is corrected by position data from the second calibration fixture. In an embodiment, a first calibration fixture is affixed to a C-arm camera and a smaller second calibration fixture is affixed to a patient. Data from the first and second calibration fixtures is used with tracking data to calibrate the image acquisition data and register reference points in image and navigation reference frames.

19 Claims, 7 Drawing Sheets

METHOD AND SYSTEM FOR IMPROVED CORRECTION OF REGISTRATION ERROR IN A FLUOROSCOPIC IMAGE

RELATED APPLICATIONS

[Not Applicable]

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

The present invention generally relates to image navigation. In particular, the present invention relates to a system and method for correcting error in registration of image and navigation references used in image-guided operations.

Medical practitioners, such as doctors, surgeons, and other medical professionals, often rely upon technology when performing a medical procedure, such as image-guided surgery or examination. A tracking system may provide positioning information for the medical instrument with respect to the patient or a reference coordinate system, for example. A medical practitioner may refer to the tracking system to ascertain the position of the medical instrument when the instrument is not within the practitioner's line of sight. A tracking system may also aid in pre-surgical planning.

The tracking or navigation system allows the medical practitioner to visualize the patient's anatomy and track the position and orientation of the instrument. The medical practitioner may use the tracking system to determine when the instrument is positioned in a desired location. The medical practitioner may locate and operate on a desired or injured area while avoiding other structures. Increased precision in locating medical instruments within a patient may provide for a less invasive medical procedure by facilitating improved control over smaller instruments having less impact on the patient. Improved control and precision with smaller, more refined instruments may also reduce risks associated with more invasive procedures such as open surgery.

Tracking systems may also be used to track the position of items other than medical instruments in a variety of applications. That is, a tracking system may be used in other settings where the position of an instrument in an object or an environment is difficult to accurately determine by visual inspection. For example, tracking technology may be used in forensic or security applications. Retail stores may use tracking technology to prevent theft of merchandise. In such cases, a passive transponder may be located on the merchandise. A transmitter may be strategically located within the retail facility. The transmitter emits an excitation signal at a frequency that is designed to produce a response from a transponder. When merchandise carrying a transponder is located within the transmission range of the transmitter, the transponder produces a response signal that is detected by a receiver. The receiver then determines the location of the transponder based upon characteristics of the response signal.

Tracking systems are also often used in virtual reality systems or simulators. Tracking systems may be used to monitor the position of a person in a simulated environment. A transponder or transponders may be located on a person or object. A transmitter emits an excitation signal and a transponder produces a response signal. The response signal is detected by a receiver. The signal emitted by the transponder may then be used to monitor the position of a person or object in a simulated environment.

Tracking systems may be ultrasound, inertial position, or electromagnetic tracking systems, for example. Electromagnetic tracking systems may employ coils as receivers and transmitters. Typically, an electromagnetic tracking system is configured in an industry-standard coil architecture (ISCA). ISCA uses three colocated orthogonal quasi-dipole transmitter coils and three colocated quasi-dipole receiver coils. Other systems may use three large, non-dipole, non-colocated transmitter coils with three colocated quasi-dipole receiver coils. Another tracking system architecture uses an array of six or more transmitter coils spread out in space and one or more quasi-dipole receiver coils. Alternatively, a single quasi-dipole transmitter coil may be used with an array of six or more receivers spread out in space.

The ISCA tracker architecture uses a three-axis dipole coil transmitter and a three-axis dipole coil receiver. Each three-axis transmitter or receiver is built so that the three coils exhibit the same effective area, are oriented orthogonally to one another, and are centered at the same point. If the coils are small enough compared to a distance between the transmitter and receiver, then the coil may exhibit dipole behavior. Magnetic fields generated by the trio of transmitter coils may be detected by the trio of receiver coils. Using three approximately concentrically positioned transmitter coils and three approximately concentrically positioned receiver coils, for example, nine parameter measurements may be obtained. From the nine parameter measurements and one known position or orientation parameter, a position and orientation calculation may determine position and orientation information for each of the transmitter coils with respect to the receiver coil trio with three degrees of freedom.

In medical and surgical imaging, such as intraoperative or perioperative imaging, images are formed of a region of a patient's body. The images are used to aid in an ongoing procedure with a surgical tool or instrument applied to the patient and tracked in relation to a reference coordinate system formed from the images. Image-guided surgery is of a special utility in surgical procedures such as brain surgery and arthroscopic procedures on the knee, wrist, shoulder or spine, as well as certain types of angiography, cardiac procedures, interventional radiology and biopsies in which x-ray images may be taken to display, correct the position of, or otherwise navigate a tool or instrument involved in the procedure.

Several areas of surgery involve very precise planning and control for placement of an elongated probe or other article in tissue or bone that is internal or difficult to view directly. In particular, for brain surgery, stereotactic frames that define an entry point, probe angle and probe depth are used to access a site in the brain, generally in conjunction with previously compiled three-dimensional diagnostic images, such as MRI, PET or CT scan images, which provide accurate tissue images. For placement of pedicle screws in the spine, where visual and fluoroscopic imaging directions may not capture an axial view to center a profile of an insertion path in bone, such systems have also been useful.

When used with existing CT, PET or MRI image sets, previously recorded diagnostic image sets define a three dimensional rectilinear coordinate system, either by virtue of their precision scan formation or by the spatial mathematics of their reconstruction algorithms. However, it may be desirable to correlate the available fluoroscopic views and anatomical features visible from the surface or in fluoroscopic images with features in the 3-D diagnostic images and with external coordinates of tools being employed. Correlation is often done by providing implanted fiducials and adding externally visible or trackable markers that may be imaged. Using a keyboard or mouse, fiducials may be identified in the various images. Thus, common sets of coordinate registration points may be identified in the different images. The common sets of coordinate registration points may also be trackable in an automated way by an external coordinate measurement device, such as a suitably programmed off-the-shelf optical tracking assembly. Instead of imageable fiducials, which may for example be imaged in both fluoroscopic and MRI or CT images, such systems may also operate to a large extent with simple optical tracking of the surgical tool and may employ an initialization protocol wherein a surgeon touches or points at a number of bony prominences or other recognizable anatomic features in order to define external coordinates in relation to a patient anatomy and to initiate software tracking of the anatomic features.

Generally, image-guided surgery systems operate with an image display which is positioned in a surgeon's field of view and which displays a few panels such as a selected MRI image and several x-ray or fluoroscopic views taken from different angles. Three-dimensional diagnostic images typically have a spatial resolution that is both rectilinear and accurate to within a very small tolerance, such as to within one millimeter or less. By contrast, fluoroscopic views may be distorted. The fluoroscopic views are shadowgraphic in that they represent the density of all tissue through which the conical x-ray beam has passed. In tool navigation systems, the display visible to the surgeon may show an image of a surgical tool, biopsy instrument, pedicle screw, probe or other device projected onto a fluoroscopic image, so that the surgeon may visualize the orientation of the surgical instrument in relation to the imaged patient anatomy. An appropriate reconstructed CT or MRI image, which may correspond to the tracked coordinates of the probe tip, may also be displayed.

Among the systems which have been proposed for effecting such displays, many rely on closely tracking the position and orientation of the surgical instrument in external coordinates. The various sets of coordinates may be defined by robotic mechanical links and encoders, or more usually, are defined by a fixed patient support, two or more receivers such as video cameras which may be fixed to the support, and a plurality of signaling elements attached to a guide or frame on the surgical instrument that enable the position and orientation of the tool with respect to the patient support and camera frame to be automatically determined by triangulation, so that various transformations between respective coordinates may be computed. Three-dimensional tracking systems employing two video cameras and a plurality of emitters or other position signaling elements have long been commercially available and are readily adapted to such operating room systems. Similar systems may also determine external position coordinates using commercially available acoustic ranging systems in which three or more acoustic emitters are actuated and their sounds detected at plural receivers to determine their relative distances from the detecting assemblies, and thus define by simple triangulation the position and orientation of the frames or supports on which the emitters are mounted. When tracked fiducials appear in the diagnostic images, it is possible to define a transformation between operating room coordinates and the coordinates of the image.

In general, the feasibility or utility of a system of this type depends on a number of factors such as cost, accuracy, dependability, ease of use, speed of operation and the like. Intraoperative x-ray images taken by C-arm fluoroscopes alone have both a high degree of distortion and a low degree of repeatability, due largely to deformations of the basic source and camera assembly, and to intrinsic variability of positioning and image distortion properties of the camera. In an intraoperative sterile field, such devices are typically draped, which may impair optical or acoustic signal paths of the signal elements they employ to track the patient, tool or camera.

More recently, a number of systems have been proposed in which the accuracy of the 3-D diagnostic data image sets is exploited to enhance accuracy of operating room images, by matching these 3-D images to patterns appearing in intraoperative fluoroscope images. These systems may use tracking and matching edge profiles of bones, morphologically deforming one image onto another to determine a coordinate transform, or other correlation process. The procedure of correlating the lesser quality and non-planar fluoroscopic images with planes in the 3-D image data sets may be time-consuming. In techniques that use fiducials or added markers, a surgeon may follow a lengthy initialization protocol or a slow and computationally intensive procedure to identify and correlate markers between various sets of images. All of these factors have affected the speed and utility of intraoperative image guidance or navigation systems.

Correlation of patient anatomy or intraoperative fluoroscopic images with precompiled 3-D diagnostic image data sets may also be complicated by intervening movement of the imaged structures, particularly soft tissue structures, between the times of original imaging and the intraoperative procedure. Thus, transformations between three or more coordinate systems for two sets of images and the physical coordinates in the operating room may involve a large number of registration points to provide an effective correlation. For spinal tracking to position pedicle screws, the tracking assembly may be initialized on ten or more points on a single vertebra to achieve suitable accuracy. In cases where a growing tumor or evolving condition actually changes the tissue dimension or position between imaging sessions, further confounding factors may appear.

When the purpose of image guided tracking is to define an operation on a rigid or bony structure near the surface, as is the case in placing pedicle screws in the spine, the registration may alternatively be effected without ongoing reference to tracking images, by using a computer modeling procedure in which a tool tip is touched to and initialized on each of several bony prominences to establish their coordinates and disposition, after which movement of the spine as a whole is modeled by optically initially registering and then tracking the tool in relation to the position of those prominences, while mechanically modeling a virtual representation of the spine with a tracking element or frame attached to the spine. Such a procedure dispenses with the time-consuming and computationally intensive correlation of different image sets from different sources, and, by substituting optical tracking of points, may eliminate or reduce the number of x-ray exposures used to effectively determine the tool position in relation to the patient anatomy with the reasonable degree of precision.

However, each of the foregoing approaches, correlating high quality image data sets with more distorted shadowgraphic projection images and using tracking data to show tool position, or fixing a finite set of points on a dynamic anatomical model on which extrinsically detected tool coordinates are superimposed, results in a process whereby machine calculations produce either a synthetic image or select an existing data base diagnostic plane to guide the surgeon in relation to current tool position. While various jigs and proprietary subassemblies have been devised to make each individual coordinate sensing or image handling system easier to use or reasonably reliable, the field remains unnecessarily complex. Not only do systems often use correlation of diverse sets of images and extensive point-by-point initialization of the operating, tracking and image space coordinates or features, but systems are subject to constraints due to the proprietary restrictions of diverse hardware manufacturers, the physical limitations imposed by tracking systems and the complex programming task of interfacing with many different image sources in addition to determining their scale, orientation, and relationship to other images and coordinates of the system.

Several proposals have been made that fluoroscope images be corrected to enhance their accuracy. This is a complex undertaking, since the nature of the fluoroscope's 3D to 2D projective imaging results in loss of a great deal of information in each shot, so the reverse transformation is highly underdetermined. Changes in imaging parameters due to camera and source position and orientation that occur with each shot further complicate the problem. This area has been addressed to some extent by one manufacturer which has provided a more rigid and isocentric C-arm structure. The added positional precision of that imaging system offers the prospect that, by taking a large set of fluoroscopic shots of an immobilized patient composed under determined conditions, one may be able to undertake some form of planar image reconstruction. However, this appears to be computationally very expensive, and the current state of the art suggests that while it may be possible to produce corrected fluoroscopic image data sets with somewhat less costly equipment than that used for conventional CT imaging, intra-operative fluoroscopic image guidance will continue to involve access to MRI, PET or CT data sets, and to rely on extensive surgical input and set-up for tracking systems that allow position or image correlations to be performed.

Thus, it remains highly desirable to utilize simple, low-dose and low cost fluoroscope images for surgical guidance, yet also to achieve enhanced accuracy for critical tool positioning.

Magnetic and gravitational fields affect x-rays and other image energy sources. Focal length and piercing point of x-rays may change depending upon the position of a C-arm or other mobile component of an imaging system. A difference between an imaging angle and an angle of the Earth's magnetic field may cause distortion that affects a resulting image. Additionally, an operator or patient may bump the C-arm or other component of an imaging system during operation or positioning, which may affect a resulting image. Thus, there is a need for improved calibration to reduce an effect of distortion on an image.

Registration is a process of correlating two coordinate systems, such as a patient image coordinate system and an electromagnetic tracking coordinate system. Several methods may be employed to register coordinates in imaging applications. "Known" or predefined objects are located in an image. A known object includes a sensor used by a tracking system. Once the sensor is located in the image, the sensor enables registration of the two coordinate systems.

U.S. Pat. No. 5,829,444 by Ferre et al., issued on Nov. 3, 1998, refers to a method of tracking and registration using a headset, for example. A patient wears a headset including radiopaque markers when scan images are recorded. Based on a predefined reference unit structure, the reference unit may then automatically locate portions of the reference unit on the scanned images, thereby identifying an orientation of the reference unit with respect to the scanned images. A field generator may be associated with the reference unit to generate a position characteristic field in an area. When a relative position of a field generator with respect to the reference unit is determined, the registration unit may then generate an appropriate mapping function. Tracked surfaces may then be located with respect to the stored images.

However, registration using a reference unit located on the patient and away from the fluoroscope camera introduces inaccuracies into coordinate registration due to distance between the reference unit and the fluoroscope. Additionally, the reference unit located on the patient is typically small or else the unit may interfere with image scanning. A smaller reference unit may produce less accurate positional measurements, and thus impact registration.

Typically, a reference frame used by a navigation system is registered to an anatomy prior to surgical navigation. Registration of the reference frame impacts accuracy of a navigated tool in relation to a displayed fluoroscopic image. Therefore, a system and method that improve registration of the reference frame would be highly desirable. Improved registration may help to decrease error between reference frames and improve navigated tracking accuracy.

Thus, there is a need for a system and method for improved registration of image and navigation references used in image-guided operations.

BRIEF SUMMARY OF THE INVENTION

Certain embodiments of the present invention provide a method and system for improved registration of image and navigation references used in image-guided operations. Certain embodiments of the system include an image acquisition device for obtaining at least one image of an object, a first calibration fixture positioned in relation to the image acquisition device, and a second calibration fixture positioned in relation to the object. The first calibration fixture is used to obtain position data in relation to the image acquisition device. The second calibration fixture is used to obtain position data in relation to the object.

In an embodiment, the first calibration fixture is used to form a characterization the image acquisition device, and the second calibration fixture is used to refine the characterization. The first calibration fixture may also be larger than the second calibration fixture. In an embodiment, the first calibration fixture and the second calibration fixture include a plurality of radiopaque markers, such as ball bearings. In an embodiment, the image acquisition device comprises a camera positioned on a C-arm, and the object may be a patient. The system may also include at least one tracking device for obtaining at least one of position and orientation data for at least one of the first calibration fixture and the second calibration fixture. The system may additionally include a tool manipulated by an operator using images obtained by the image acquisition device.

Certain embodiments of the method include acquiring data from a first calibration target located near an image acquisition device, calibrating the image acquisition device using data from the first calibration target, acquiring data from a second calibration target located near an object being imaged, and refining the image acquisition device using data from the second calibration target. In an embodiment, the data from the first calibration target and the data from the second calibration target are acquired at substantially a same time for use in calibrating the image acquisition device. The calibrating step may also include calibrating the image acquisition device using the data in a Tsai projection model.

In an embodiment, the method further includes acquiring at least one of position and orientation measurement using at least one tracking device located on at least one of the first calibration device and the second calibration device. The method may also include modeling the image acquisition device. The image acquisition device may also be characterized to improve registration between points in an image reference frame and points in a navigation reference frame.

Certain embodiments of a method for improved registration of image and navigation references include acquiring characterization data from a first calibration fixture and a second calibration fixture positioned in relation to an image acquisition device in an image reference space, obtaining position data from at least one tracking device associated with at least one of the first calibration fixture and the second calibration fixture in a navigation reference space, and modeling the image acquisition device using the characterization data in the image reference space and the position data in the navigation reference space. In an embodiment, the method also includes acquiring a plurality of images of an object using the image acquisition device, obtaining position data from a tracking device affixed to a tool in relation to the image acquisition device, registering the position data in the image reference space defined by the plurality of images, and correcting the registered position data using the characterization data.

The modeling step may include modeling the image acquisition device using a projection model. Additionally, the first calibration fixture and the second calibration fixture may include a plurality of radiopaque markers. The image acquisition device may include a camera positioned on a C-arm. The first calibration fixture may be larger than the second calibration fixture, for example.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

Figure 1:
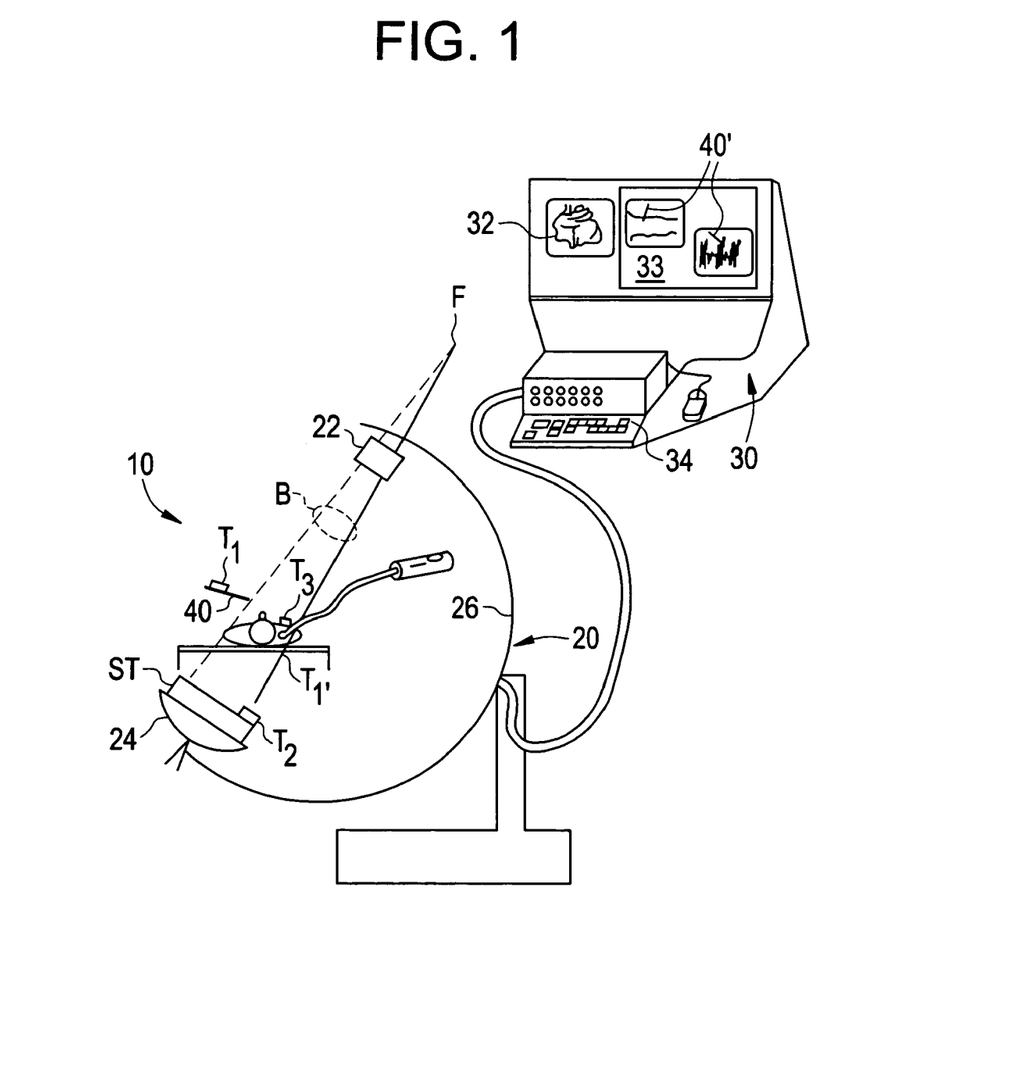
FIG. 1 illustrates an imaging system in accordance with an embodiment of the present invention for use in an operating room environment.

FIG. 1 illustrates an imaging system 10 in accordance with an embodiment of the present invention for use in an operating room environment. As shown in FIG. 1, the system 10 includes a fluoroscope 20, a work station 30 having one or more displays 32 and a keyboard/mouse or other user interface 34, and a plurality of tracking elements T1, T2, T3. The fluoroscope 20 is illustrated as a C-arm fluoroscope in which an x-ray source 22 is mounted on a structural member or C-arm 26 opposite to an x-ray receiving and detecting unit, referred to herein as an imaging assembly 24. The C-arm moves about a patient or other object to produce two dimensional projection images of the patient from different angles. The patient or object remains positioned between the source and the camera, and may, for example, be situated on a table or other support, although the patient/object may move. The tracking elements, described further below, are mounted such that one element T1 is affixed to, incorporated in or otherwise secured against movement with respect to a surgical tool or probe 40. A second tracking unit T2 is fixed on or in relation to the fluoroscope 20, and a third tracking unit T3 fixed on or in relation to the patient. The surgical tool may be a rigid probe as shown in FIG. 1, allowing the tracker T1 to be fixed at any known or convenient position, such as on its handle, or the tool may be a flexible tool, such as a catheter, flexible endoscope or an articulated tool, for example. In the latter cases, the tracker T1 is preferably a small, localized element positioned in or at the operative tip of the tool as shown by catheter tracker T1' in FIG. 1, to track coordinates of the tip within the body of the patient.

In an embodiment, a fluoroscope operates with an x-ray source 22 positioned opposite the camera or image sensing assembly 24. While in some systems, the X-ray source is fixed overhead, and the camera is located below a patient support, the discussion below will be illustrated with regard to the more complex case of a typical C-arm fluoroscope, in which the source and camera are connected by a structural member, the C-arm, that allows movement of the source and camera assembly about the patient so that the C-arm may be positioned to produce x-ray views from different angles or perspectives. In such C-arm devices, the imaging beam generally diverges at an angle, the relative locations and orientations of the source and camera vary with position due to structural flexing and mechanical looseness, and the position of both the source and the camera with respect to the patient and/or a tool which it is desired to track may also vary in different shots.

The imaging beam illustrated by B in FIG. 1 diverges from the source 22 in a generally truncated conical beam shape, and the C-arm 26 is movable along a generally arcuate path to position the source and camera for imaging from different directions. This generally involves positioning the camera assembly 24 as close as possible behind the relevant tissue or operating area of the patient, while the C-arm assembly is moved roughly about a targeted imaging center to the desired viewing angle. The C-arm or other beam structure 26 may be a somewhat flexible structure, subject to bending, deflection or sagging as the source and camera move to different positions around the patient, and the C-arm may also have other forms of dimensional variation or looseness, such as drive gear backlash, compressible elastomeric suspension components or the like, which may contribute to variations and non-repeatability of the relative disposition and alignment of the source and camera with respect to each other, and with respect to the patient, as the assembly is moved to different positions. The C-arm may also move eccentrically or translationally to allow better clearance of the patient support table. The bending deflections of the C-arm assembly may vary the actual position of the source 22 by almost a centimeter or more with respect to the image detector, and may displace the source 22 from a nominal position which may be indicated, for example, by an encoder present in the fluoroscope stand or C-arm positioning assembly.

Figure 2:
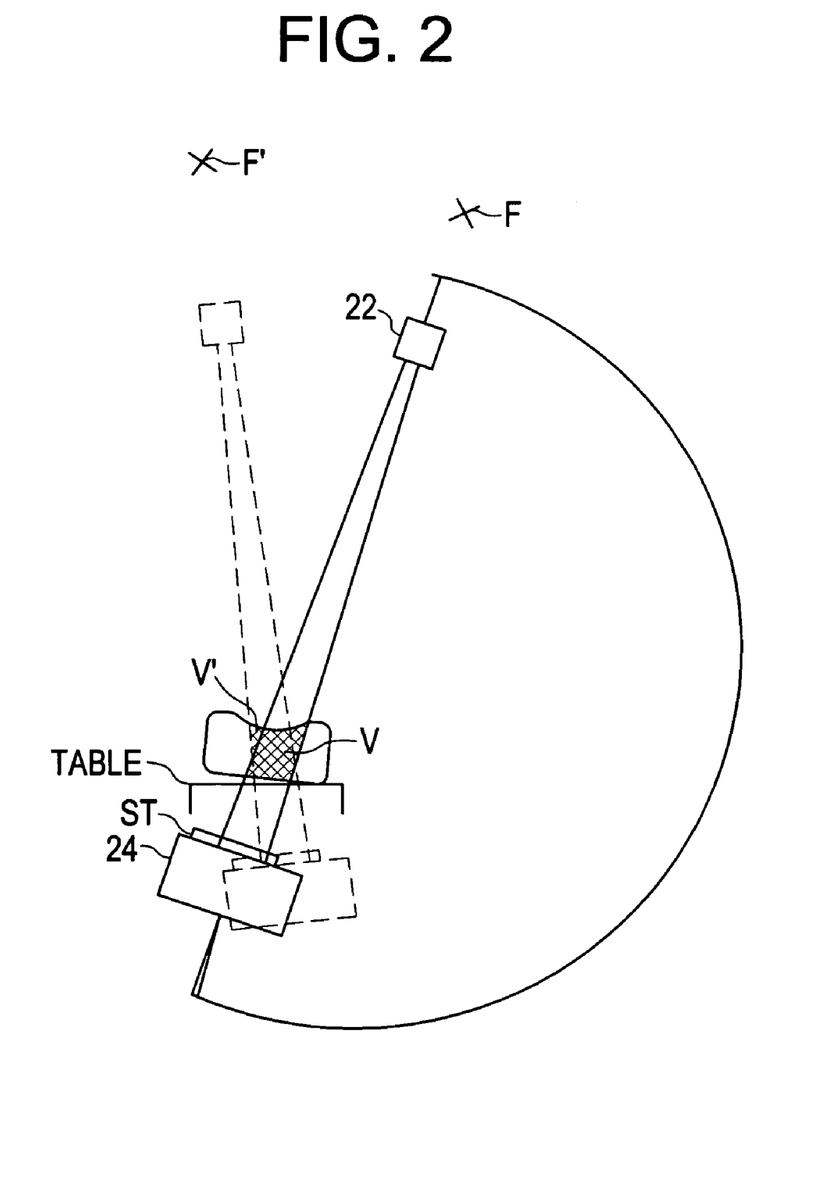
FIG. 2 illustrates the fluoroscope in two different imaging positions, with a first position shown in solid line, and a second position in dashed line phantom.

FIG. 2 illustrates the fluoroscope 20 in two different imaging positions, with a first position shown in solid line, and a second position in dashed line phantom. In the first position, a tissue volume V is imaged with a divergent beam from the above right, and a virtual beam origin or focal point at F, while the image from the second position catches a largely overlapping but partly distinct tissue volume with a divergent beam from the upper left, and a different focal point F'. The distances from points F, F' to the camera may be different, and the camera itself may shift and tilt with respect to the beam and its center axis, respectively. In practice, the x-ray beam is generally aimed by its center ray, whose intersection with the imaging plane, referred to as the piercing point, may be visually estimated by aiming the assembly with a laser pointing beam affixed to the source. The x-ray beam may be considered to have a virtual origin or focal point F at the apex of the cone beam. Generally, the camera assembly 24 is positioned close to the patient, but may be subject to constraints posed by the operating table, the nature of the surgical approach, and tools, staging, clamps and the like, so that imaging of a tissue volume somewhat off the beam center line, and at different distances along the beam, may occur. As noted above, flexing of the C-arm also changes the distance to the focal point F and this also may slightly vary the angular disposition of the beam to the camera, so this shifting geometry may affect the fluoroscope images.

Furthermore, the camera 24 may utilize an image sensing unit that itself introduces further distortions into the received distribution of image radiation. For example, the unit may involve a detector that employs a phosphor surface of generally curved contour to convert the x-ray image intensity distribution to a free electron distribution. Such a curved phosphor screen is generally placed over an electron multiplier or image intensifier assembly that provides an enhanced output video signal, but may further introduce a form of electron optical distortion that depends upon the intensifier geometry and varies with the orientation of the camera assembly in the earth's magnetic field. Other configurations of image detectors are also known or proposed, such as digital x-ray detectors or flat semiconductor arrays, which may have different imaging-end fidelity characteristics. Deflection or physical movement of the camera itself as well as electron/optical distortion from the camera geometry, image detector and variations due to gravitational, magnetic or electromagnetic fields may enter image reception and affect projective geometry and other distortion of a final image produced by the assembly.

Aspects of imaging system variability may be addressed using tracking elements in conjunction with a calibration fixture or correction assembly to provide fluoroscopic images of enhanced accuracy for tool navigation and workstation display. The calibration fixture and use of the calibration fixture in tracking are described in further detail in U.S. Pat. No. 6,484,049 by Seeley et al., issued on Nov. 19, 2002, and U.S. Pat. No. 6,490,475 by Seeley et al., issued on Dec. 3, 2002, which are herein incorporated by reference in their entirety. A reference unit may also be used, as described in further detail in U.S. Pat. No. 5,829,444 by Ferre et al., issued on Nov. 3, 1998, which is herein incorporated by reference.

In an embodiment, a plurality of calibration fixtures or reference units may be used to reduce registration error for a registration or reference frame and improve accuracy in navigated tracking of an instrument. A reference frame may include a calibration fixture. The calibration fixture may be removably attached in a precise position with respect to the camera or to the patient. One or more tracking elements or sensors may be included in the calibration fixture. A tracking element may be a point-origin defining tracking element that identifies spatial coordinates and/or orientation of the tracking element and, therefore, an object to which the tracking element is attached. Thus, a tracking element may with one or more measurements determine a position of markers in the calibration fixture and a position and orientation of the fixture itself or a surface to which the fixture is attached.

Figure 3:
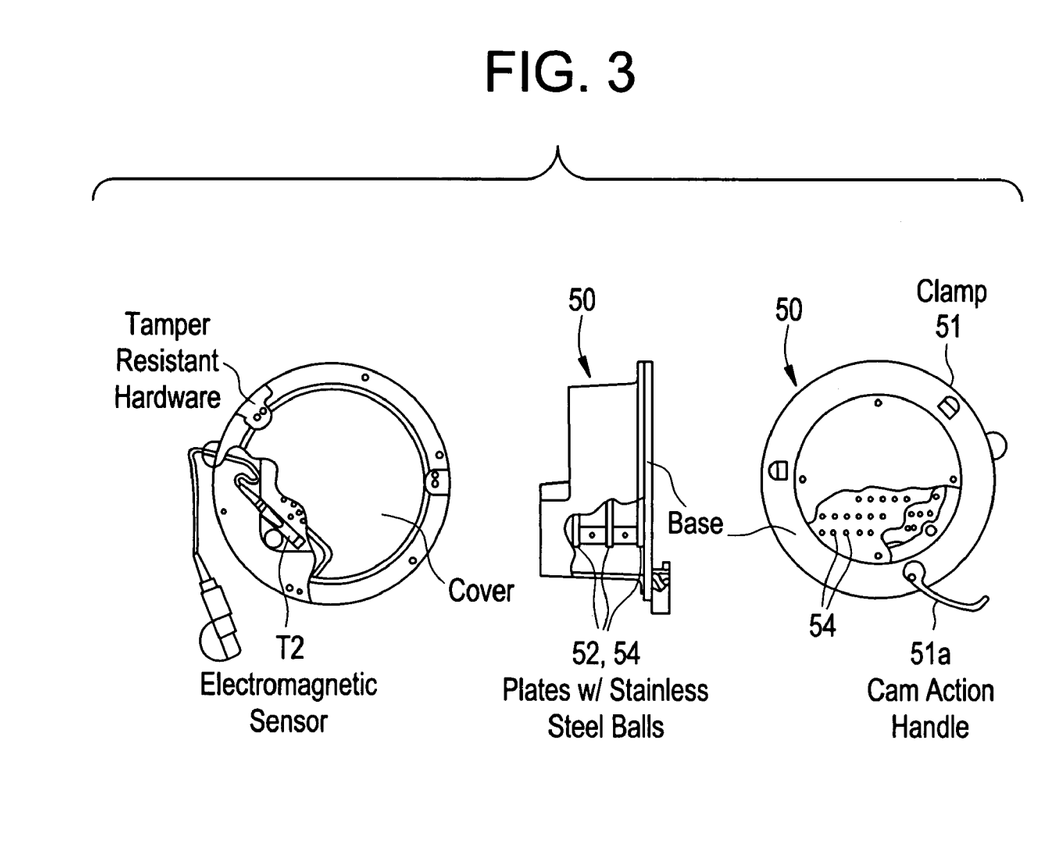
FIG. 3 illustrates an embodiment of a calibration fixture used in accordance with an embodiment of the present invention.

FIG. 3 illustrates an embodiment of a first calibration fixture 50, marker array, or standard ST used in accordance with an embodiment of the present invention. The fixture 50 may include one or more marker plates or sheets 52 of radiolucent material, such as an acrylic (e.g., Lexan) or polymer plate. Each sheet holds an array of radiopaque point-like markers 54, such as stainless steel balls (e.g., ball bearings or BBs). The one or more plates holding the BBs may be affixed at or near to the face of the camera imaging assembly so as to allow accurate calibration of the entire volume of interest while occupying a sufficiently small space that the camera may be positioned closely to the patient. The illustrated calibration fixture 50 includes a releasable clamp assembly 51, with a clamp handle 51a, or other attachment device configured to attach directly on or over the face of the camera assembly. Additionally, the calibration fixture 50 may include an attachment point for a tracking sensor. The structure of the calibration fixture 50 is predefined and modeled to serve as a reference. That is, radiopaque markers, sensors, and/or other structures in the calibration fixture 50 are located and measured during manufacturing or prior to use in imaging. Characterization data from the structure of the calibration fixture 50 is used to register the image and navigation coordinate systems. For example, characterization data describing reference markers in the fixture 50 is loaded into a tracking system prior to scanning. Tight manufacturing tolerances and/or modeling are used to model the first calibration fixture 50 as a reliable reference to measure and correct registration error.

Figure 4:
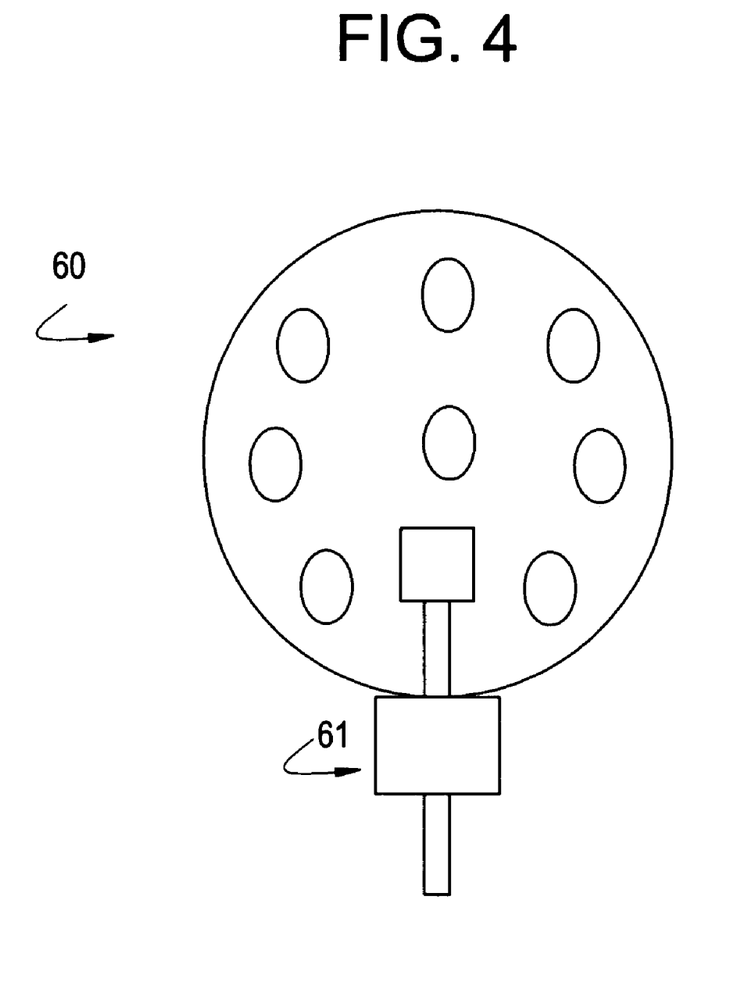
FIG. 4 illustrates an embodiment of a calibration fixture used in accordance with an embodiment of the present invention.

FIG. 4 illustrates an embodiment of a second calibration fixture 60 used in accordance with an embodiment of the present invention. The calibration fixture 60 may be affixed at or near an object being imaged, such as a patient. The calibration fixture 60 includes an attachment point 61 for a tracking sensor. The calibration fixture 60 includes an array of radiopaque calibration markers, such as BBs. In an embodiment, a size of the second calibration fixture 60 is minimized to reduce an impact of the fixture 60 on a resulting image. Holes or openings, for example, may also be left in the calibration fixture 60, as shown in FIG. 4, to reduce its profile and impact on imaging. The structure of the second calibration fixture 60 is predefined and modeled to serve as a reference. That is, radiopaque markers, sensors, and/or other structures in the calibration fixture 60 are located and measured during manufacturing or prior to use in imaging. Characterization data from the structure of the calibration fixture 60 is used to register the image and navigation coordinate systems. For example, characterization data describing reference markers in the fixture 60 is loaded into a tracking system prior to scanning. Tight manufacturing tolerances and/or modeling are used to model the first calibration fixture 50 as a reliable reference to measure and correct registration error.

The BBs or other radiopaque or calibration markers may be of different sizes in the different planes or may be of the same size. In an embodiment, the BBs are of the same size, e.g., about one or two millimeters in diameter. The BBs or other markers appear in an image and are discernable from anatomy or other interesting objects.

In an embodiment, a radiopaque object, such as a metal or other material object, for example a BB, may be placed into holes on a radiolucent marker sheet such that all marker coordinates are known. Alternatively, marker plates may be manufactured by circuit board microlithography techniques to provide desired patterns of radiopaque markers, for example as metallization patterns, on one or more thin radiolucent films or sheets. The calibration fixtures 50, 60 may also be fabricated as a single block of a suitable radiolucent material with holes drilled to accommodate BBs or other markers. BBs or other markers may be arranged at multiple levels and multiple positions in the fixture.

One suitable radiolucent material is a structural foam of the type used in aircraft wings for lightweight structural rigidity. The radiolucent material may also be employed in separate thin marker-holding sheets. In an embodiment, the selected polymer or foam, and the number and size of the markers, are configured to remain directly in the imaging beam of the fluoroscope device and be imaged in each shot, while the position of the fixture is tracked. The fixture materials are selected to avoid introducing any significant level of x-ray absorption or x-ray scattering by the plates, sheets or block, and the size and number of markers are similarly chosen to avoid excessive shadowing of the overall image, while maintaining a sufficiently dense image level for their detectability, so that both the imaging source radiation level and the resulting image density scale remain comparable to currently desired operating levels. In an embodiment, BBs or other markers are arranged in a pattern at one or more levels, with a different pattern at each level. Further, when more than one array at different depths is used, the patterns may be positioned so that as the source/camera alignment changes, BBs of one pattern cast shadows substantially distinct from those of the other pattern(s).

Thus, the first and second calibration fixtures 50, 60 are predefined structures known with respect to a tracker. In an embodiment, the first and second calibration fixtures 50, 60 serve as one effective calibration target to measure and correct registration error between coordinate systems. A combination of the first and second fixtures 50, 60 creates a larger volume within which to characterize and virtually model the camera. Positions of the calibration markers in the fixtures 50, 60 are known with respect to each other. Data obtained from the second calibration fixture 60 may be used to refine data obtained from the first calibration fixture 60, for example.

Figure 5:
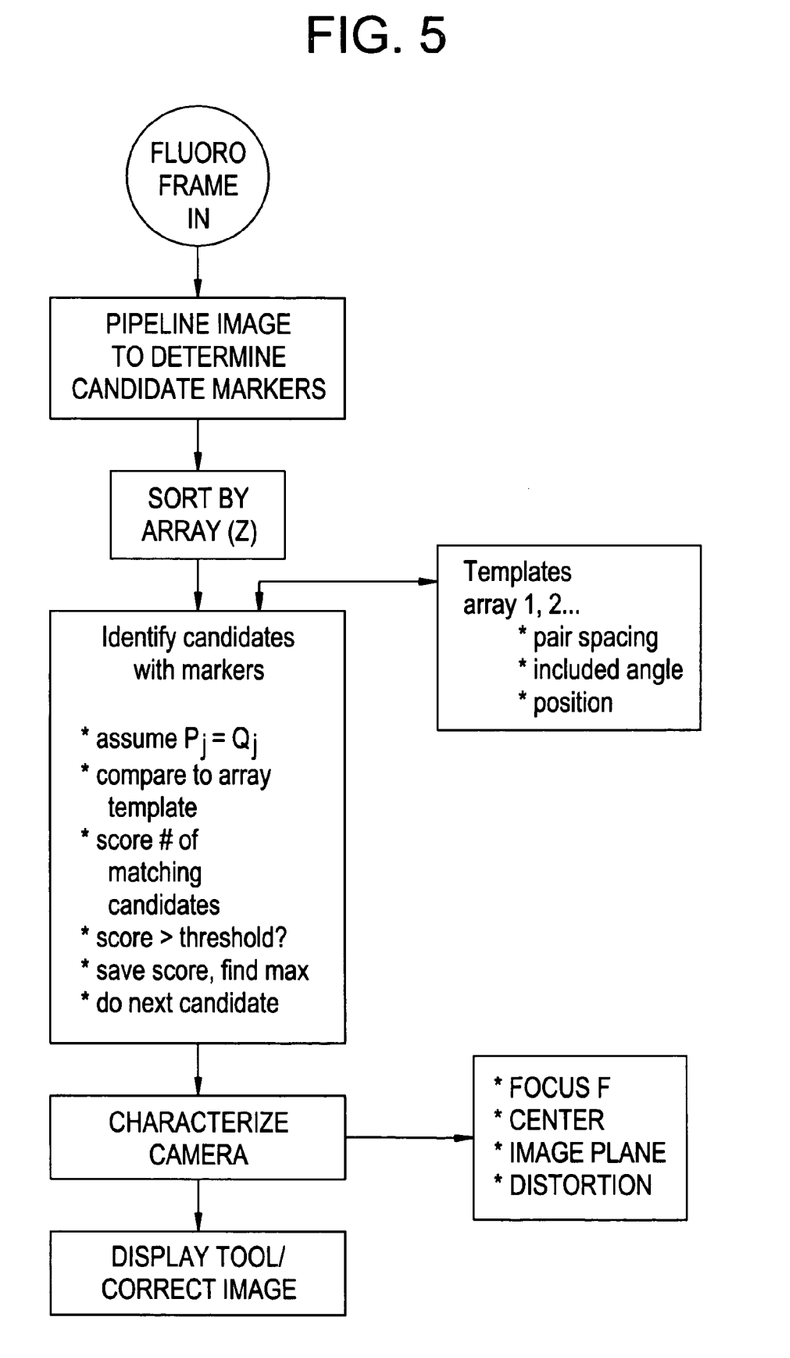
FIG. 5 depicts an operation of a tracking system used in accordance with an embodiment of the present invention.

FIG. 5 depicts an operation of a tracking system used in accordance with an embodiment of the present invention. Initially, as noted above, a tracking element is associated with each of the tool, the patient and the fluoroscope, for example. Each tracking element may be secured against movement with respect to the structure it is tracking, but the structure may be free to move. Thus, the fluoroscope may move freely about the patient, and both the patient and the tool may move within the operative field. In an embodiment, the tracking element associated with the fluoroscope is positioned on a calibration fixture 50 which is itself rigidly affixed to the camera of the fluoroscope as described above. The calibration fixture 50 may be removably attached in a precise position, and the tracking element T2 may be held in a rigid oriented body affixed to the fixture 50. The tracking element T2 may, for example, be a point-origin defining tracking element that identifies the spatial coordinates and orientation of its housing, hence, with a rigid coordinate transform, also specifies the position and orientation coordinates of the object to which it is attached. Thus, the tracking element T2 may with one measurement determine the positions of all markers in the calibration fixture, and the position and orientation of the fixture itself or the horizontal surface of the camera assembly. The second calibration fixture 60 may be positioned with respect to the patient, to fine-tune measurements obtained using the first calibration fixture 50.

For example, a plurality of fluoroscopic images may be obtained of an upper leg of a sawbone model. A portion of an anatomy, such as a femoral head and trochanter, is visible in the images. An object is mounted at the level of the model. The object is a predefined structure including a transmitter and radiopaque markers, such as BBs (for example, 10 BBs). Positional information regarding the radiopaque markers may be collected using one or more tracking sensors. Positional information regarding the radiopaque markers may also be collected in a navigation reference space using a tool, such as a short pointer, and an image-guided surgery system, such as a FluoroTrak™ navigation system, running in a field service mode, for example. BBs from a calibration fixture mounted at the level of the model, for example, are visible in the images. In an embodiment, images may be taken at a plurality of angles wherein the BBs are located by a navigation system in an image reference space. A detected error may be determined from a distance between collected locations in the navigation space (e.g., a two- or three-dimensional space).

In an embodiment, a Tsai projection model or other similar model is used to locate BBs or other radiopaque objects in a calibration target with respect to a patient space of a fluoroscopic image. The Tsai model is described by Roger Tsai in his article on 3-D camera calibration published in the IEEE Journal of Robotics and Automation, Volume RA-3, No. 4, August 1987, pp. 323–344. A navigation system uses a transmitter affixed to a patient anatomy and a receiver in a calibration target to establish a navigation reference. BBs at the level of the patient may be incorporated into the Tsai model to improve registration between image and navigation reference frames.

The Tsai model is a camera model based on a pin hole or point source model of perspective projection. The Tsai model may be used to predict a position of a point in two-dimensional pixel coordinates based on a position of the point in three-dimensional coordinates. For example, a point source of light is projected against a black screen. An object is placed between the point source of light and the black screen to determine qualities of a camera imaging the object. A diverse (e.g., larger geometry) object improves accuracy in characterization of the camera. However, an object's geometric size in a light beam is balanced against interference with motion of components in a system.

The Tsai model uses 11 parameters: five internal and six external parameters. The internal parameters are used to describe how a camera forms an image. The external parameters are used to depict a position and orientation of the camera in a reference coordinate frame. Internal parameters include an effective focal length of a pin hole camera, a first order radial lens distortion coefficient, coordinates of a center of radial lens distortion, and a scale factor to account for uncertainty due to horizontal scanline resampling. External parameters include rotation angles for a transform between image and navigation reference coordinate frames and translational components for the transform between image and navigation reference coordinate frames.

In operation, camera imaging parameters are characterized while addressing distortion in each image frame or shot of a C-arm fluoroscope. Then, the parameters are used to reconstruct a three-dimensional volume that is dynamically referenced to a patient and a tool or instrument being used. Finally, the dynamically referenced three-dimensional volume is fused with preoperative volumetric data.

Equipment and procedure used in characterizing camera parameters and volume construction includes two primary components, a first component provided by a tracking assembly which determines position of a fluoroscope calibration fixture relative to one or both of the tool and patient body, and a second component provided by a processor operating on each image that characterizes or models the geometry of the camera and performs all subsequent processing. Camera modeling is facilitated by providing one or more calibration fixtures that include an array of markers, which are either tracked as a rigid unit or affixed to the camera, while the imaged position of the markers in each fluoroscope shot serves to characterize the imaging geometry so as to allow correction of imaged features at measured distances from the camera, and permit registration of successive images in different poses.

In an embodiment, when tracked relative to a tool, the surgical instrument display 40' of FIG. 1 affected by determining tool position, focus and imaging axis, and rendering the instrument in conjunction with one or more of the three types of images mentioned above. In one embodiment, the processor determines an image distortion inverse transform and projects a distorted or transformed tool graphic or image on the fluoroscopic view. In another embodiment, the processor determines the camera geometry for each image and transforms the set of fluoroscopic images such that the screen coordinates of display 33 are similar or aligned with the operating coordinates as measured by tracking elements T2, T3. The calibration results in more accurate tool tracking and representation over time. The image data of an imaging sequence for a region of tissue about a common origin may be back-projected or otherwise processed to define a three dimensional stack of fluoro-CT images, for example. Certain embodiments thus allow a relatively inexpensive C-arm fluoroscope to achieve accuracy and registration to prepare CT or other images for tool guidance and reconstruction of arbitrary planes in the imaged volume.

The camera may be calibrated using marker identification information described above. The imaging carried out by the fluoroscope is modeled as a camera system in which an optical center is located at an x-ray source and an imaging plane is located a distance F (focal length) away from the optical center inside a camera assembly. The optical axis is a line through the x-ray source and perpendicular to a horizontal face of the camera. The intersection of the optical axis and the image plane is defined as the piercing point. Certain imaging or distortion characteristics may also be measured by the array of marker images, which thus determines a corrective perspective transformation. The Tsai model or other suitable model determines radial distortion in addition to parameters using an algorithm that takes as input the matched marker and image locations, estimates of focal length and information about the number of rows and columns in the projection image. The Tsai algorithm is readily implemented with one or more planes of markers in the fixture 50 or 50'. When the fluoroscope is sufficiently rigid that focus does not vary, a single plane of markers may be used to define the camera parameters.

By providing a pattern of markers in a plane, the shifts in position of those markers in the image define a local transformation that corrects for radial distortion of the image, while non-occluding markers in two planes, or at two different positions along the z-axis are sufficient to identify the focus and the optical or center axis of the beam. Other models relying, for example, on defining a distortion morphing transformation from the array of marker images may also be applied. A pattern of markers may comprise a rectangular lattice, e.g., one marker every centimeter or half-centimeter in two orthogonal directions, or may occupy a non-periodic but known set of closely-spaced positions. The calibration fixture may be constructed such that markers fill a peripheral band around the imaged tissue, to provide marker shadow images that lie outside the imaged area and do not obscure the tissue which is being imaged for display. In an embodiment, the markers are located in the imaged field, so that the imaging camera and distortion transforms they define closely fit and characterize the geometric imaging occurring in that area. In an embodiment, the image processor removes the marker shadow-images from the fluoroscope image frame before display on the console 30 (see FIG. 1), and may interpolate or otherwise correct image values in the surrounding image.

To display a tool position on an uncorrected fluoroscope image, the processor obtains the position of the front and back tips of the tool. The tips are fixed offsets from the coordinates of the tracking element T1 associated with the tool. The tracker may also determine tool orientation relative to the patient from position and orientation relative to the tracking element T3 on the patient at the time of image capture. Tracked position coordinates are converted to be relative to the fixed tracking element on the camera, or so that all coordinates reference the image to which the camera model applies. In a basic tool navigation embodiment, the camera calibration matrix is then applied to the front and back tip position coordinates of the tool to convert them to fluoroscope image space coordinates. The end point coordinates are converted to undistorted two-dimensional image coordinates (e.g., perspective coordinates) using the calculated focal length of the camera, which are then converted to distorted two-dimensional image coordinates using the lens distortion factor derived from the matrix of marker positions. Corresponding pixel locations in the two-dimensional fluoroscope image are determined using the x-scale factor, the calculated origin of the image plane and scaling based on the number of pixels per millimeter in the camera image sensor and display. The determined position is then integrated with the video display on the fluoroscope to show a graphical representation of the tool with its front tip location in image coordinates. In an embodiment, the tool is displayed as an instrument vector, a two-dimensional line on the fluoroscopic image with a red dot representing its tip. Thereafter, during an ongoing procedure, the tracking assembly may track tool movement relative to the patient, and a processor controls the tracking and determines from the position of the tool when the integrated display is redrawn using the above-described image distortion transformations to correctly situate the displayed tool in a position on a new image.

Figure 6:
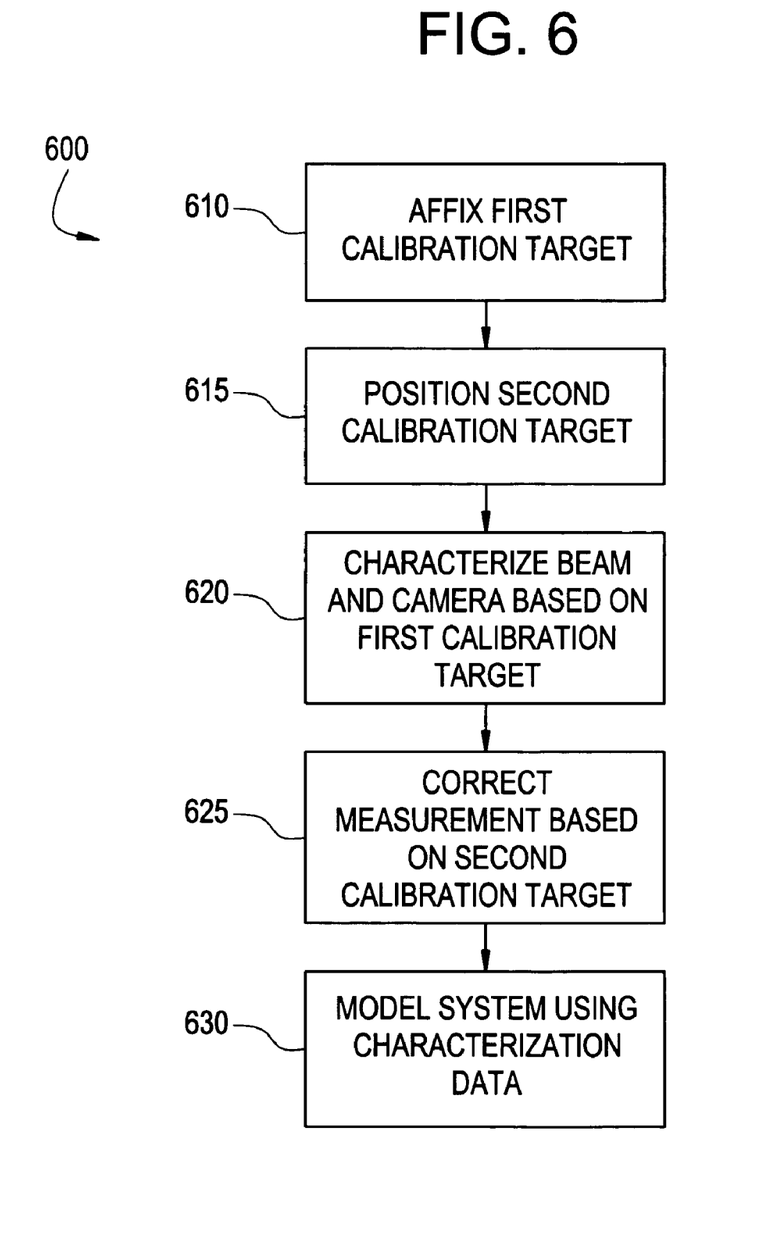
FIG. 6 illustrates a flow diagram for a method for improved registration between image and navigation reference coordinate frames used in accordance with an embodiment of the present invention.

FIG. 6 illustrates a flow diagram for a method 600 for improved registration between image and navigation reference coordinate frames used in accordance with an embodiment of the present invention. Registration involves recording scan images of a predetermined orientation and mapping the special orientation from a tracking system onto the scanned images. For example, orientations of scanned images may be in the sagittal (y-z plane), coronal (x-z plane), and/or axial (x-y plane). Scanned images may e digitally stored, and a distance between each scanned image may be recorded, as are relative orientations of each set of images.

First, at step 610, a first calibration target is affixed to an imaging system. For example, the first calibration target is affixed to a C-arm in the imaging system. An example of a first calibration target is shown in FIG. 3 and described above. Then, at step 615, a second calibration target is positioned near a patient or other object that is being imaged or upon which an operation is being performed. An example of a second calibration target is shown in FIG. 4 and described above.

Data from the first and second calibration targets may be analyzed separately and/or together. That is, first, at step 620, an x-ray or other imaging beam is characterized along with a location of a patient or object being scanned with respect to the beam based on the first calibration target affixed to the C-arm. Then, at step 625, measurement is corrected based on the second calibration target positioned near the patient/object. In an embodiment, steps 620 and 625 may be undertaken at approximately the same time.

At step 630, the imaging system or a portion of the imaging system is modeled using characterization data from the first and second calibration targets. For example, the C-arm is modeled virtually using a computer. The first and second calibration targets, with known geometric properties, are used to characterize the C-arm (the camera mounted on the C-arm). For example, focal length, piercing point, and errors from the lensing system may be determined using the calibration targets and modeled. Once a reference frame is established and image references are registered to navigation references, an object may be tracked using a navigation system, for example.

Thus, predefined structures (for example, the calibration targets) including radiopaque markers in a defined arrangement may be used to obtain characterization data (for example, position and orientation data) are used to correlate images obtained with respect to an image coordinate system and tracking data obtained with respect to a navigational coordinate system. Use of a plurality of predefined structures located in a plurality of positions improves registration and helps to minimize errors occurring when coordinates in different coordinate systems are correlated (for example, to help ensure that a coordinate in one system most closely matches a corresponding coordinate in another system). The Tsai projection model or similar projection model is used with the predefined structures to determine characterization data for the image(s).

In an embodiment, for three-dimensional imaging, registration is executed once pre-operatively to prepare for a procedure. For two-dimensional imaging, however, registration is executed upon each acquisition of a fluoroscopic image. An image may be obtained from any angle as per an operator's workflow (for example, a surgeon's workflow). A first calibration fixture is positioned in relation to an image acquisition device and data related to the first calibration fixture is obtained. A smaller second calibration fixture is positioned at the level of the patient. Data related to the first calibration fixture helps enables the second calibration fixture to be located and data obtained relative to the second calibration fixture. Data related to the second calibration fixture refines and improves a correlation solution obtained using the first calibration fixture. For example, the second calibration fixture provides position/orientation information that enables corresponding coordinates in the navigational and imaging coordinate systems to be more closely matched.

Figure 7:
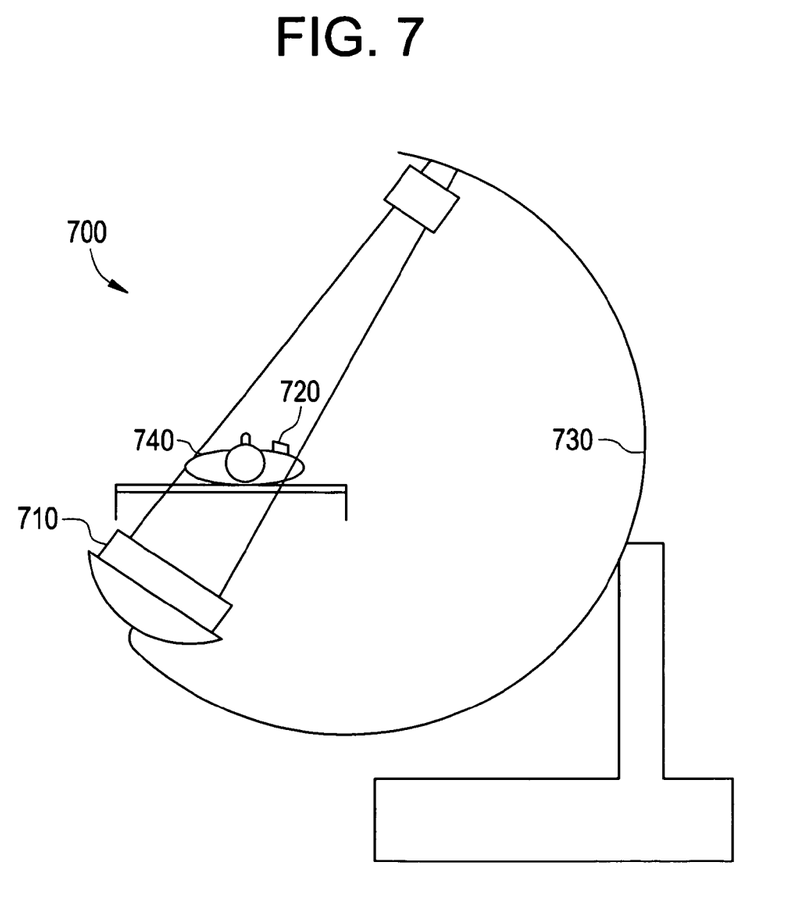
FIG. 7 illustrates a fluoroscopic imaging and navigation system used in accordance with an embodiment of the present invention.

FIG. 7 illustrates a fluoroscopic imaging and navigation system 700 used in accordance with an embodiment of the present invention. The system 700 includes a first calibration target 710, a second calibration target 720, a C-arm 730, a patient 740, and a tracking system 750 (not pictured). The first calibration target 710 is positioned on or near the C-arm 730 in the vicinity of an imaging camera mounted on the C-arm 730. For example, the first calibration target 710 is bolted to the C-arm 730 near the camera. In an embodiment, the first calibration target 710 is a larger calibration fixture including BBs and/or other markers, as described above, to determine position and/or orientation information with respect to the C-arm camera. The second calibration target 720 is positioned on or near the patient 740. For example, the second calibration target 720 including a transmitter and BBs is placed on the skin of the patient 740. In an embodiment, the second calibration target 720 is a smaller calibration fixture or tracking device with BBs and/or other markers.

In an embodiment, a camera model is determined using the first calibration target 710 on the C-arm 730, and the model is tweaked by analyzing the second calibration target 720 near the patient 740. The first calibration target 710 is used to obtain data to solve the Tsai model for tracking with respect to images of the patient 740. The first calibration target 710 and objects in the target 710 have known geometries and definable positions with respect to a tracking system and reference frame. The tracking system 750 also identifies a position of the C-arm 730 to provide a common frame of reference. The smaller second calibration target 720 is used in combination with the larger first calibration target 710 to improve accuracy of the Tsai model and position and/or orientation calculations.

In another embodiment, all markers in the first and second calibration targets 710, 720 are treated as being included in a single object. Sensors are attached to both calibration targets 710, 720 to enable markers, such as BBs, in the targets 710, 720 to be associated with respect to each other. The Tsai camera model and reference frame registration may be determined using data from both calibration targets 710, 720 simultaneously.

In an embodiment, the first and/or second calibration targets 710, 720 may include a position characteristic field generator or position triangulation system that allows a sensor to receive position information regarding the target

710, 720. The field generator or triangulation system help the target 710, 720 serve as a reference for registration between coordinate systems.

The tracking system 750 may be used with a C-arm camera to facilitate image-guided surgery and other navigated operations. Typically, a transmitter, such as an electromagnetic transmitter or other transmitter, is affixed to a patient 740 or other object. In an embodiment, the transmitter is affixed to a calibration fixture 720 which is affixed to the patient/object so that patient motion and fixture position may be tracked.

In another embodiment, a transmitter is affixed to the patient 740, and a calibration fixture 720 with BBs or other markers and a receiver is positioned near the patient 740 at the time an image is obtained. That is, the calibration fixture 720 may be held by an operator or the patient 740 or affixed or laid on the patient 740. Thus, a second sensor (e.g., electromagnetic receiver) is calibrated to the position of a radiopaque geometric calibration fixture 720. Position and image information are therefore obtained.

The tracking system 750 may be used to monitor the position of an instrument or tool with respect to the calibration fixture 720. A sensor or other tracking element is attached to the instrument and the fixture 720 to allow the tracking system 750 to track the instrument in the reference frame. Changes in instrument position are correlated with spatial orientation of stored images of the patient 740. Thus, for example, as a surgeon moves a medical instrument, images being obtained appear on a display in response to the position of the medical instrument. Therefore, the surgeon is able to access coronal, sagittal, and axial views associated with a location of a tip of the instrument regardless of whether the tip is inside of the patient 740.

In an embodiment, the first and second calibration targets 710, 720 may be used with ultrasound imaging to characterize an ultrasound imager in real time. For example, a CT or MR imaging study may be obtained with markers on the patient 740. The markers are used in the images to model the ultrasound imager.

In another embodiment, when an updated x-ray image, for example, is taken of the patient 740, characterization of the camera or imager is performed because each image is affected by the position of the C-arm 730. Magnetic and gravitational fields affect x-rays and other image energy sources. Focal length and piercing point of x-rays may change by centimeters, for example, depending upon the position of the C-arm. A difference between an imaging angle and an angle of the Earth's magnetic field may cause distortion that affects a resulting image. Additionally, an operator or patient may bump the C-arm or other component of an imaging system during operation or positioning, which may affect a resulting image. Thus, calibrating the system after an image is obtained helps to reduce an effect of distortion on the image.

Thus, certain embodiments incorporate a reference on a C-arm of an imaging system and a reference close to an operating arm of the imaging system to characterize the C-arm camera. Characterization information is used to improve registration between points in an image reference frame and points in a navigation reference frame. Multiple calibration fixtures provide measurements near the camera or image sensing assembly and measurements near the patient or object being imaged. In an embodiment, a larger, more complex calibration target may be positioned near the camera while a smaller, less obtrusive calibration target is positioned near the patient to fine tune measurements from the larger calibration target while minimizing interference with image data of the patient. Multiple calibration fixtures form a single, larger effective calibration target to measure and correct registration between coordinate systems. Multiple calibration fixtures improve accuracy of modeling, measurement, and characterization of an imaging device, such as a C-arm camera.

Thus, certain embodiments reduce potential sources of cumulative errors and simplify the task of registering and transforming to common coordinates. Operators are therefore able to more precisely track and display a tool in real time, and to produce accurate fluoro-CT images using a C-arm fluoroscope.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A system for improved registration of image and navigation references used in image-guided operations, said system comprising:
   an image acquisition device for obtaining at least one image of an object;
   a first calibration fixture positioned in relation to said image acquisition device, wherein said first calibration fixture is used to obtain position data in relation to said image acquisition device; and
   a second calibration fixture positioned in relation to said object, wherein said second calibration fixture is used to obtain position data in relation to said object,
   wherein said fimi and second calibration fixtures include a plurality of radiopaque markers, and
   wherein said first calibration fixture is used to form a characterization of said image acquisition device and said second calibration fixture is used to refine said characterization.

2. The system of claim 1 wherein said first calibration fixture is larger than said second calibration fixture.

3. The system of claim 1 wherein said plurality of radiopaque markers includes ball bearings.

4. The system of claim 1 whack said image acquisition device comprises a camera positioned on a C-arm.

5. The system of claim 1 wherein said object comprises a patient.

6. The system of claim 1 further comprising at least one tracking device for obtaining at least one of position and orientation data for at least one of said first calibration fixture and said second calibration fixture.

7. The system of claim 1 further comprising a tool manipulated by an operator using images obtained by said image acquisition device.

8. A method for improved calibration of an image acquisition system, sad method comprising:
   acquiring data from a first calibration target located near an image acquisition device, wherein said first calibration target includes a first plurality of radiopaque markers;
   calibrating said image acquisition device using data from said first calibration target;

acquiring data from a second calibration target located near an object being imaged, wherein said second calibration target includes a second plurality of radiopaque markers; and refining said calibration of said image acquisition device using data from said second calibration target.

9. The method of claim 8, wherein said data from said first calibration target and said data from said second calibration target are acquired at substantially a same time for use in calibrating said image acquisition device.

10. The method of claim 8, wherein said calibrating step further comprises calibrating said image acquisition device using said data in a Tsai projection model.

11. The method of claim 8, further comprising acquiring at least one of position and orientation measurement using at least one tracking device located on at least one of said first calibration device and said second calibration device.

12. The method of claim 8, further comprising modeling said image acquisition device.

13. The method of claim 8, further comprising characterizing said image acquisition device to improve registration between points in an image reference frame and points in a navigation reference frame.

14. A method for improved registration of image and navigation references, said method comprising:

acquiring characterization data from a first calibration fixture and a second calibration fixture positioned in relation to an image acquisition device in an image reference space, wherein said first and second calibration fixtures include a plurality of radiopaque markers;

obtaining position data Thorn at least one tracking device associated with al least one of said first calibration fixture and said second calibration fixture in a navigation reference space; and modeling said image acquisition device using said characterization data in said image reference space and said position data in said navigation reference space.

15. The method of claim 14, further comprising:

acquiring a plurality of images of an object using said image acquisition device;

obtaining position data from a tacking device affixed to a tool in relation to said image acquisition device;

registering said position data in said image reference space defined by said plurality of images; and correcting said registered position data using said characterization data.

16. The method of claim 14, wherein said modeling step further comprises modeling said image acquisition device using a projection model.

17. The method of claim 14, wherein said plurality of radiopaque markers includes a plurality of ball bearings.

18. The method of claim 14, wherein said image acquisition device comprises a camera positioned on a C-arm.

19. The method of claim 14, wherein said first calibration fixture is larger than said second calibration fixture.

* * * * *

UNITED STATES PATENT AND TRADEMARK OFFICE
CERTIFICATE OF CORRECTION

PATENT NO. : 7,097,357 B2 Page 1 of 1
APPLICATION NO. : 10/859767
DATED : August 29, 2006
INVENTOR(S) : Douglas Karl Johnson and Lewis J. Levine It is certified that error appears in the above-identified patent and that said Letters Patent is hereby corrected as shown below:

In col. 18, claim 1, line 38, delete "fimi" and insert --first--;
In col. 20, claim 14, line 1, delete "Thorn" and insert --from--;
In col. 20, claim 15, line 12, delete "tacking" and insert --tracking--.

Signed and Sealed this

Thirteenth Day of October, 2009

David J. Kappos
*Director of the United States Patent and Trademark Office*